(12) United States Patent
Ren et al.

(10) Patent No.: US 8,426,385 B2
(45) Date of Patent: *Apr. 23, 2013

(54) PHARMACEUTICAL COMPOSITION COMPRISING CYCLODEXTRIN PACLITAXEL INCLUSION AND PREPARATION METHOD THEREOF

(75) Inventors: Yong Ren, Jiangsu (CN); Jianfeng Gao, Jiangsu (CN); Shuqin Yu, Jiangsu (CN); Ling Wu, Jiangsu (CN)

(73) Assignee: Hainan Hdeton Science and Technology Co. Ltd. (CN)

( * ) Notice: Subject to any disclaimer, the term of this patent is extended or adjusted under 35 U.S.C. 154(b) by 232 days.

This patent is subject to a terminal disclaimer.

(21) Appl. No.: 12/440,792

(22) PCT Filed: Oct. 13, 2006

(86) PCT No.: PCT/CN2006/002693
§ 371 (c)(1),
(2), (4) Date: Mar. 11, 2009

(87) PCT Pub. No.: WO2008/031286
PCT Pub. Date: Mar. 20, 2008

(65) Prior Publication Data
US 2010/0041625 A1 Feb. 18, 2010

(30) Foreign Application Priority Data

Sep. 12, 2006 (CN) .......................... 2006 1 0041530
Oct. 13, 2006 (WO) ................ PCT/CN2006/002693

(51) Int. Cl.
C08B 37/16 (2006.01)
A61K 31/715 (2006.01)

(52) U.S. Cl.
USPC ............................................ 514/58; 514/449

(58) Field of Classification Search ........................ None
See application file for complete search history.

(56) References Cited

U.S. PATENT DOCUMENTS

| | | | |
|---|---|---|---|
| 5,684,169 | A | 11/1997 | Hamada et al. |
| 5,804,568 | A | 9/1998 | Rubinfeld |
| 6,218,374 | B1 | 4/2001 | Rubinfeld |
| 6,284,746 | B1 | 9/2001 | Szente et al. |
| 2004/0053888 | A1 | 3/2004 | Suzuki |
| 2005/0009783 | A1 | 1/2005 | Kagkadis |
| 2007/0087999 | A1 | 4/2007 | Geczy |
| 2009/0012042 | A1 | 1/2009 | Ren et al. |
| 2010/0048685 | A1 | 2/2010 | Ren et al. |
| 2011/0015145 | A1* | 1/2011 | Bodor ............................ 514/46 |

FOREIGN PATENT DOCUMENTS

| | | |
|---|---|---|
| CA | 2092979 | 3/1993 |
| CA | 2123946 | 5/1994 |
| CN | 1222321 | 7/1999 |
| CN | 1424112 | 6/2003 |
| CN | 1440748 | 9/2003 |
| CN | 200510095176 | * 11/2005 |
| EP | 1950227 A1 | * 7/2008 |
| WO | 9924073 | 5/1999 |
| WO | WO 9924073 A1 | * 5/1999 |
| WO | 03043602 | 5/2003 |

OTHER PUBLICATIONS

U.S. Appl. No. 12/440,942, filed Mar. 12, 2009.
Guchelaar et al.; Clinical, Toxicological and Pharmaceutical Aspects of the Antineoplastic Drug Taxol: A Review; Clinical Oncology 1994, pp. 41-48.
Cserhati et al.; Interaction of Taxol and Other Anticancer Drugs With Hydroxypropyl-B-Cyclodextrin; International Journal of Pharmaceutics 1994; pp. 70-75.
Yue et al.; Inclusion Complex of Paclitaxel in Hydroxypropyl-B-Cyclodextrin; Chem. Res. Chinese U. 2005; pp. 750-752.
Dordunoo et al.; Solubility and Stability of Taxol: Effects of Buffers and Cyclodextrins; International Journal of Pharmaceutics 1996; pp. 192-201.
Sharma et al.; Pharmaceutical and Physical Properties of Paclitaxel (Taxol) Complexes With Cyclodextrins; Journal of Pharmaceutical Sciences, vol. 84, No. 10, Oct. 1995; pp. 1223-1230.
Moser et al.; Taxol Inclusion Complexes With a Cyclodextrin Dimer: Possibilities to Detoxify Chemotherapeutics and to Target Drugs Specifically to Tumors?; Journal of Inclusion Phenomena and Macrocyclic Chemistry 2001; pp. 13-18.
Alcaro et al.; Preparation, Characterization, Molecular Modeling and In Vitro Activity of Paclitaxel—Cyclodextrin Complexes; Bioorganic & Medicinal Chemistry Letters 2002; pp. 1637-1641, 2002(12): 1637-1641.
Fossella, Frank V.; Single-Agent Docetaxel in Patients With Refractory Non-Small-Cell Lung; Dept. of Medical Oncology, The University of Texas M.D. Anderson Cancer Center; 8 pp, Oncology 1997;11(7 Suppl.):11-15.
Miller et al.; Phase II Trial of a 75-MG/M2 Dose of Docetaxel With Prednisone Premedication for Patients With Advanced Non-Small Cell Lung Cancer; Thoracic Oncology Service, Division of Solid Tumor Oncology, Dept. of Medicine; pp. 968-972, Cancer, 1995, 75(4) : 968-972.

(Continued)

Primary Examiner — Sreeni Padmanabhan
Assistant Examiner — Svetlana M Ivanova
(74) Attorney, Agent, or Firm — Schmeiser, Olsen & Watts, LLP

(57) ABSTRACT

A pharmaceutical composition comprising cyclodextrin/paclitaxel inclusion, which consists of paclitaxel, cyclodextrin and a pharmaceutically acceptable excipient, wherein the mass ratio of the paclitaxel to cyclodextrin is 1:10-150, the said cyclodextrin is hydroxylpropyl-sulfobutyl-7-β-cyclodextrin, or sulfobutylether-7-β-cyclodextrin, or their mixture; the stability constant of the cyclodextrin/paclitaxel inclusion is Ka=5396M−1−1412M−1. The preparation method of the pharmaceutical composition is as follow: (a) A solution of cyclodextrin is added dropwise to a solution of paclitaxel in ethanol. (b) The resulting mixture is filtered through microporous membrane of 0.2-0.4 μm after being dissolved. (c) Ethanol is removed under reduced pressure to give a liquid inclusion which has the ethanol level of less than 2%, or alternatively water is also removed under reduced pressure, the resulting product is dried giving a solid inclusion.

9 Claims, 3 Drawing Sheets

OTHER PUBLICATIONS

Grosse, P.Y.; In Vitro Modulation of Doxorubicin and Docetaxel Antitumoral Activity by Methyl-B-Cyclodextrin; European Journal of Cancer, vol. 34, No. 1, pp. 168-174, 1998.

Cao, Feng et al.; Progress in Hydrolysis of Carboxylic Esters Using Artificial Enzymes Cyclodextrins; Chinese Journal of Organic Chemistry, vol. 22, 2002, pp. 827-834.

Loftsson, Thorsteinn et al; Expert Opinion: Cyclodextrins in Drug Delivery; University of Iceland, 2005; pp. 335-351.

Medicine Forefront, Chinese Medicine Science and Technology Press, 2001: 17 pages.

Study on the Inclusion of Phenylpropanol/B2Cyclodextrin; Journal of China Pharmaceutical University, 2005, pp. 13-17.

Guidelines for Research Techniques of Chemicals Stimulation, Hypersensitivity and Hemolysis Tests, State Food and Drug Administration, Mar. 18, 2005, 31 pages.

Technical Requirements of Traditional Chinese Medicine Injection Study, State Food and Drug Adminstration, 1999, 5 pages.

Cao, Yuhua et al.; Study on Voltammetric Behavior of EU-VB6 and EU-VB6-GLY Complexes; China Academic Journal Electronic Publishing House; 2002, vol. 20, No. 6, 5 pages.

Xiaohua, Huang; Synthesis and Characterization of the Ternary Rare Earth Complex on Dysprosium—Glycine—Vitamineb; Journal of Suzhou Railway Teachers College, vol. 14, No. 4, Aug. 1997; 5 pages.

Cyclodextrin Chemistry, Science Press 2001, 3 pages.

Office Action (Mail Date Apr. 14, 2011) for U.S. Appl. No. 12/440,792, filed Mar. 11, 2009.

Office Action (Mail Date Aug. 24, 2011) for U.S. Appl. No. 12/440,792, filed Mar. 11, 2009.

Office Action (Mail Date Jan. 25, 2012) for U.S. Appl. No. 12/440,792, filed Mar. 11, 2009.

* cited by examiner

PHARMACEUTICAL COMPOSITION COMPRISING CYCLODEXTRIN PACLITAXEL INCLUSION AND PREPARATION METHOD THEREOF

FIELD OF THE INVENTION

The present invention relates to a pharmaceutical composition, particularly relates to a pharmaceutical composition comprising cyclodextrin/paclitaxel inclusion, which consists of paclitaxel, hydroxypropyl-sulfobutyl-β-cyclodextrin or sulfobutyl-β-cyclodextrin and a pharmaceutically acceptable excipient and the preparation method thereof.

BACKGROUND OF THE INVENTION

Paclitaxel (trade name: Taxol) is a diterpenoid compound extracted from *Taxus brevifolia* barks, with its molecular formula $C_{47}H_{51}NO_{24}$ and molecular weight 853.92, chemical name: (2S,5R,7S,10R,13S)-10,20-bi(acetoxy)-2-benzoyl-oxy-1,7-dihydroxy-9-oxo-5,20-epoxy taxanes-11-ene-13-radical(3S)-3-benzoyl amino-3-phenyl-D-lactic acid ester. Paclitaxel is a white or similar white crystalline powder, has relatively stable chemical properties at the condition of pH 4~8. This product has a higher fat-solubility (log P.O/w=3.5), almost insoluble in water. According to different literatures, its solubility in water is within the range of 0.25 μg/ml~0.60 μg/ml, difficult soluble in many commonly-used pharmaceutical solvents. A number of pharmacological tests show that, paclitaxel has a significant effect on advanced ovarian cancer, metastatic breast cancer and melanoma and has high curative rate on refractory ovarian cancer and metastatic breast cancer, has good prospects on the treatment of prostate cancer, gastrointestinal cancer, small cell lung cancer and non-small cell lung cancer. So it is one of the anti-cancer drugs with the highest anti-cancer effect discovered at present.

Because of difficult absorption through oral taking (oral absorption rate: 2%~4%), paclitaxel is administered through injection in clinical application. The existing paclitaxel oral injection is prepared into a colorless viscous concentrated solution (containing 30 mg paclitaxel in 5 ml of solution) with polyoxyethylene castor oil and anhydrous alcohol in a ratio of 1:1 (V/V). When using this product, the concentrated solution is firstly diluted into a 500 mL 0.9% sodium chloride injection or 5% glucose injection liquid or 5% dextran injection liquid. After diluted into a solution containing 0.06 mg/ml paclitaxel (solvent content of 0.5%~1.0%), the mixed solution is added by intravenous infusion for 3~24 h after filtered through a filter of 0.22 μm diameter.

The infusion dose is 135~175 mg/m$^{-2}$ and the maximum tolerance infusion dose is 225~240 mg/m$^{-2}$ within 3 h.

Paclitaxel injection uses polyoxyethylene castor oil/anhydrous ethanol as solvent, having a high incidence of clinical allergic reaction. When used, allergic reaction prevention treatment should be conducted by oral administration of 10 mg dexamethasone 12 h and 6 h before drug administration and intramuscular injection of 20 mg diphenhydramine and intravenous injection of 300 mg cimetidine or 50 mg ranitidine 30~60 min before drug administration. Those patients who have allergic reactions are injected with epinephrine for treatment. In addition, the paclitaxel injection cannot be prepared, stored and injected with PVC plastic containers or injection containers so as to prevent from reaction between solvents and containers, which may generate other allergens. The diluent solution is stored in a glass or polypropylene plastic container or in a special polyester injection device. Although the sensitization mechanism of paclitaxel injection is still unclear, the same allergic reactions occurred in another two drugs (cyclosporine and Teniposide) adopting this solvent and tests also confirmed that castor oil itself can cause dog's histamine release and hypotension (Clinical Oncology, 1994; 6: 40), therefore, the allergenicity of solvent castor oil also becomes the research focus. In recent years, the study of high efficiency and low toxicity of drug carrier containing no castor oil and new paclitaxel administration technology has become the research hot spot.

At present, researches about paclitaxel administration technology mainly focus on liposomes, combined solvents, cyclodextrin, emulsions, nanoparticles, chelation, microspheres and other technologies. Because of the special molecule inclusion function of cyclodextrin and the clinical application of injection cyclodextrin derivatives, researches on cyclodextrin-paclitaxel inclusion technology has made rapid progress. At present, the main types of cyclodextrin used to paclitaxel preparations improvement include: acetyl-γ-cyclodextrin, hydroxypropyl-β-cyclodextrin, hydroxypropyl-γ-cyclodextrin, bridged Bis(β-cyclodextrin), γ-cyclodextrin, succinyl-methyl-β-cyclodextrin, anionic-β-cyclodextrin polymer and so on. Among them, α-cyclodextrin and hydroxypropyl-β-cyclodextrin are the cyclodextrin type materials that have been clinically used to a variety of clinical drug injection preparations, but at present, clinical applications of other cyclodextrins have not been reported yet.

Because of the special structural properties of cyclodextrin and special requirements of paclitaxel application, the valuable cyclodextrin-paclitaxel system should be reflected in such research areas as inclusion reaction, solubilization rate, pharmaceutical stability, chemical stability, paclitaxel activity and side effect changes after inclusion, etc. Although paclitaxel has a larger molecular volume, researches show that cyclodextrin still has a varying degree of inclusion with paclitaxel, and the inclusion reaction degree is directly related to specific reaction conditions such as solvent, temperature, material type especially the type of cyclodextrin structure and proportion of materials, etc. Therefore, different conclusions can be made if taking varying research methods. Thin Layer Chromatography is adopted to determine the changes of $R_f$ values of 23 kinds of anti-cancer drugs before and after adding hydroxypropyl-β-cyclodextrin (inclusion) (International Journal of Pharmaceutics, 1994, 108:69-75) and calculate the migration retention value Rm:

$$R_m = \log(1/R_f - 1)$$

Where, Rm stands for the function of drug, mobile phase and cyclodextrin concentration. When its relation curve is extended to zero (no mobile phase and cyclodextrin), the absolute migration retention value Rmo of the inclusion is obtained (if methanol concentration of the mobile phase=0, cyclodextrin concentration=0, then Rm=Rmo, the smaller Rmo is, the greater the change of inclusion migration property is and the greater the inclusion reactions). The results show that, among the 23 drugs, the inclusion reaction of paclitaxel is weakest (maximum Rmo). Further tests with α-cyclodextrin of smaller molecular cavity) showed that, paclitaxel also presented the weakest inclusion ability (Journal of Pharmaceutical & Biomedical Analysis, 1995, 13:533-541); but, the UV spectrum study (Chem. Res. Chinese U. 2005, 21: 749-752) showed that, hydroxypropyl-β-cyclodextrin/paclitaxel in the aqueous solution presented a stronger inclusion reaction, with the inclusion constant up to 3030 M$^{-1}$, mainly presenting dual inclusion reaction; Phase solubility studies showed that (International Journal of Pharmaceutics, 1996, 133: 191-201), paclitaxel has multiple inclusion with cyclodextrin primarily by dual inclusion, and the dual-inclusion constants of γ-cyclodextrin, hydroxypropyl-γ-cyclodextrin and hydroxypropyl-β-cyclodextrin were 785 $M^{-1}$, $1886M^{-1}$ and $7965M^-$ respectively, showing that hydroxypropyl-β-cyclodextrin/paclitaxel has strong inclusion ability. It is also discovered that, after adding organic solvent such as alcohols, the inclusion constants substantially increased and the paclitaxel solubility also significantly improved. In the pure water, cyclodextrin has a better solubilization effect on paclitaxel, and the paclitaxel solubility in about 50% hydroxypropyl-β-cyclodextrin aqueous solution can be up to 3.4 mg/ml (J Pharm Sci, 1995, 84; 1223-1229), which is the best results currently reported. If tetraethylenepentamine bridged bis(β-cyclodextrin) is used, the solubilization of paclitaxel can be up to 2.0 mg/ml (CN1440748). Cyclodextrin solubilization is associated with the proportion of paclitaxel-cyclodextrin in addition to the types of cyclodextrin.

After inclusion, the paclitaxel stability enhanced and its activity has also improved. Fluorescence spectroscopy studies showed that bridged bis(β-cyclodextrin) with cyclodextrin distance of 16.1 Å has an inclusion constant as high as $10^7M^{-1}$ compared with β-cyclodextrin/paclitaxel, and the prepared molecules of ratio of 1:1 was more stable than inclusions but the paclitaxel composition has no changes. After inclusion, the drug-tumor cell reaction time was significantly extended (Journal of Inclusion Phenomena and Macrocyclic Chemistry, 2001, 39: 13-18); Studies showed that, because the increased paclitaxel solubility can improve the extracellular concentration of paclitaxel, conducive to the permeation of drugs through cell membranes, the cyclodextrin solubilization could maintain or enhance the activity of paclitaxel (Bioorganic & Medicinal Chemistry Letters, 2002, 12:1637-1641); After paclitaxel was added to cyclodextrin, a stable preparations solution containing a small amount of organic solvents or additives could be prepared (HU P9701945; CN1281373/ZL98811010.5). In 1:50 cyclodextrin solution, the paclitaxel solubility reached 1.5 mg/ml. The inclusion complex prepared by acetyl-β-cyclodextrin or hydroxypropyl-β-cyclodextrin could significantly reduce the cardiovascular and respiratory side effects of existing paclitaxel preparations (polyoxyethylene castor oil/anhydrous ethanol solvent). Studies also showed that, inclusion reaction could also reduce side effects of paclitaxel itself (U.S. Pat. No. 6,218,374; U.S. Pat. No. 5,804,568). Animal tests showed that, use of paclitaxel inclusion complex injection prepared by hydroxypropyl-β-cyclodextrin could reduce the tissue damages of the injection parts by ⅔ compared with the paclitaxel preparations dissolved in ethanol.

There are a variety of technological inventions on the improvement of paclitaxel injection by using cyclodextrin. CN1589157 (US2005009783) discloses a paclitaxel/hydroxypropyl-β-cyclodextrin composition and the preparation method thereof. For the invention, the paclitaxel was dissolved in ethanol by a ratio of 45 g hydroxypropyl-β-cyclodextrin, 30 mg paclitaxel and 100 ml water, then added to the hydroxypropyl-β-cyclodextrin aqueous solution to prepare inclusion complex. However, a mass ratio of paclitaxel/cyclodextrin as high as 1:1500 is difficult for clinical application; HU P9701945 adopted a lower proportion of cyclodextrin, but the reported solubilization effect was not significant; U.S. Pat. No. 6,284,746 discloses an example, under the example, 11.6 mg paclitaxel and 4 g 2,6-dimethyl-β-cyclodextrin was used to prepare an inclusion complex and the paclitaxel solubilization was up to 0.9-1.0 mg/ml; U.S. Pat. No. 5,684,169 discloses that a high proportion of a variety of cyclodextrins were added with a large amount of organic solvents such as methanol, acetonitrile, ethyl acetate unsuitable for drug use. HU71251 discloses that a variety of cyclodextrins in a molar ratio of 1-20 could only allow paclitaxel solubilization to 0.05 mg/ml; HU65835 discloses that a 20 times of molar ratio (about 31 times of mass ratio) of branched cyclodextrin could allow paclitaxel solubilization to about 0.32 mg/ml.

Although studies on paclitaxel/cyclodextrin inclusion are very active, no paclitaxel/cyclodextrin inclusion is sold in the markets and the safety problems of cyclodextrin is one of the main reasons. At present, it is proved that only three dextrins and cyclodextrin derivatives including α-cyclodextrin, hydroxypropyl-β-cyclodextrin and methyl-butyl-β-cyclodextrin can be used for injection (Expert Opin Drug Deliv, 2005 March; 2(2):335-51). Among the paclitaxel preparation modification studies, more researches focus on hydroxypropyl-β-cyclodextrin, while no researches on sulfobutyl-β-cyclodextrin have been reported. For other cyclodextrins, because of no sufficient safety data, their actual technological applications are relatively higher. The major disadvantages of prior arts are: low solubility of paclitaxel (without significant cyclodextrin solubilization effect), poorer pharmaceutical stability and precipitation after dilution, higher proportion of paclitaxel/cyclodextrin, high proportion of residual organic solvents, too high cyclodextrin concentration failing to meet the basic requirements of paclitaxel preparations, etc. Selection of new cyclodextrin types with excellent performance and carrying out inclusion technology systematic research are the new methods to change such a state.

SUMMARY OF THE INVENTION

The present invention is to overcome the difficulties of paclitaxel/cyclodextrin inclusion complex study of prior arts, including low solubility of paclitaxel), poor pharmaceutical stability, higher proportion of paclitaxel/cyclodextrin, high proportion of residual organic solvents, etc., realize technological breakthrough of this field, and provide a kind of stable paclitaxel/cyclodextrin inclusion complex of higher solubility of paclitaxel and pharmaceutical stability, lower proportion of cyclodextrin and low residual organic solvents to realize clinical applications. The present invention also provides the preparation method of this inclusion complex.

For the present invention, the pharmaceutical composition comprising cyclodextrin/paclitaxel inclusion, which consists of paclitaxel, cyclodextrin and a pharmaceutically acceptable excipient. Wherein the mass ratio of paclitaxel to cyclodextrin is 1:10~150, the said cyclodextrin is hydroxypropyl-sulfobutyl-β-cyclodextrin, or sulfobutyl-β-cyclodextrin, or their mixture; the stability constant of the cyclodextrin/paclitaxel inclusion is $Ka=5396M^{-1}\sim14121M^{-1}$.

Specifically, the said pharmaceutical composition comprising cyclodextrin/paclitaxel inclusion is prepared as follow:
In the pure aqueous solution of hydroxypropyl-sulfobutyl-β-cyclodextrin, or sulfobutyl-β-cyclodextrin, or their mixture, a solution of paclitaxel in ethanol is added dropwise while stirring (or mix cyclodextrin, paclitaxel and pure water firstly, then add with ethanol solution until the whole system is dissolved, this is an equivalent step of same effect);
The resulting mixture is filtered through microporous membrane of 0.2~0.4 um;
Ethanol is removed under reduced pressure to give a liquid inclusion;
Or after ethanol is removed under reduced pressure, water is also removed under reduced pressure, the resulting product is dried giving a solid inclusion.

The resulting pharmaceutical composition comprising cyclodextrin/paclitaxel inclusion contains the ethanol level of less than 2%.

In the present invention, sulfobutyl-β-cyclodextrin or hydroxypropyl-sulfobutyl-β-cyclodextrin is added with paclitaxel solution containing appropriate amount of ethanol under the aqueous solution condition. The ethanol can promote the inclusion reaction, after removal of ethanol from the resulting inclusion (the ethanol residual level of less than 2%), a stable paclitaxel/cyclodextrin inclusion compound is obtained. The resulting inclusion is compounded with the common excipient to prepare an inclusion pharmaceutical composition for clinical use, and thus improving the paclitaxel solubility, increasing stability and reducing side effects to obtain valuable paclitaxel products for clinical applications. Preparation of inclusion complex is the key technology of the present invention.

Among the cyclodextrin derivatives for injection purpose currently available in the markets, hydroxypropyl-β-cyclodextrin is a neutral non-ionized derivative, sulfobutyl-β-cyclodextrin is an ionized derivative, and the pharmaceutical sulfobutyl-β-cyclodextrin is a product of 6-7 substitutes ($SBE_7$-β-CD, trade name Captisol). A large number of studies showed that (Medicine Development, Chinese Medicine Science and Technology Press, 2001:46-59), sulfobutyl-β-cyclodextrin has a significant improvement of pharmaceutical safety, stability, drug solubilization and production and preparation technology, etc. Its advantages include high water-solubility (>50 g/100 g $H_2O$); strong inclusion performance; no pharmacological activity; no effect on renal function; used for oral and non-oral formulations; low GMP production cost and wider ranges of uses. Under the present invention, the researched and developed hydroxypropyl-sulfobutyl-β-cyclodextrin(HP-SBE-β-CD) is a new cyclodextrin derivative substituted by hydroxypropyl group and sulfobutyl group (CN1800221A). The product has an excellent performance and high safety after preliminary tests. For the present invention, (mass ratio 1:10~150) sulfobutyl-β-cyclodextrin or hydroxypropyl-sulfobutyl-β-cyclodextrin is used to modify the paclitaxel preparations, and the obtained inclusion complex of low ratio of 1:25 (mass ratio) could enable the paclitaxel solubility as high as 9~10 mg/ml, and the solid inclusion complex can be maintained for more than 12 h stably even after diluted for 500 times, with stable chemical properties, high pharmaceutical stability, low stimulation and important application values.

Under the present invention, the preparation method of pharmaceutical composition comprising cyclodextrin/paclitaxel inclusion is as follows:

In the pure aqueous solution of hydroxypropyl-sulfobutyl-β-cyclodextrin, or sulfobutyl-β-cyclodextrin, or their mixture, a solution of paclitaxel in ethanol is added dropwise while stirring (or mix cyclodextrin, paclitaxel and pure water firstly, then add with ethanol solution until the whole system is dissolved, this is an equivalent step of same effect);

The resulting mixture is filtered through microporous membrane of 0.2~0.4 um;

Ethanol is removed under reduced pressure to give a liquid inclusion;

Or after ethanol is removed under reduced pressure, water is also removed under reduced pressure, the resulting product is dried giving a solid inclusion.

The said cyclodextrin/paclitaxel inclusion contains the ethanol level of less than 2%.

More preferably and specifically, the detailed steps for preparation of pharmaceutical composition comprising cyclodextrin/paclitaxel inclusion are as follows:

The paclitaxel and cyclodextrin in a weight ratio of 1:25 were used to prepare pure aqueous solution of cyclodextrin. The solution prepared with hydroxypropyl-sulfobutyl-β-cyclodextrin, or sulfobutyl-β-cyclodextrin, or their mixture and 2~10 times of pure water (in weight) was added with the mixed solution prepared by paclitaxel and ethanol in a weight ratio between 1:1 and 1:10, depending on dissolution of paclitaxel, while heating and stirring at room temperature or at a temperature of 25~65° C. After the inclusion formed, filtered through microporous membrane of 0.2-0.4 um; then the ethanol was removed under reduced pressure to give a liquid inclusion; or continued to reduce pressure until water was removed. The resulting product was dried under a vacuum condition to obtain a solid inclusion.

The resulting solid inclusion has a high water-solubility, easily dissolved without adding other cosolvents. The aqueous solution prepared has less side effect of hemolysis, suitable for clinical use. The solid inclusion containing 30 mg of paclitaxel of clinical dosage was added with 10-500 times of injection saline solution to prepare a solution, which could remain stable after a few days.

The said solid inclusion and commonly-used injectable medicinal excipient solution were diluted to appropriate concentration before subjecting to sterilization treatment. The resulting composition solution can be used for injection.

Validation of Inclusion Reaction:

By comparing the results of raw material sulfobutyl-β-cyclodextrin and inclusion $H,C$—COSY($^{13}C$, $^1H$ relevant spectrum) dissolved in $D_2O$, the H-3 and H-5 protons (δ4.1-3.4) within the cyclodextrin glucose loop of the inclusion were significantly moved to high electrical field (FIG. 1), which indicated that the benzoyl side-chain group of the paclitaxel molecule was included into the cyclodextrin.

UV spectrum test showed that, in the aqueous solution, the UV absorption of paclitaxel would vary with the change of the cyclodextrin (without absorption of cyclodextrin itself) concentration (FIG. 2).

Cyclodextrin structure is characterized by a high electron density of hydrophobic cavity ("Cyclodextrin Chemistry", Science Press 2001, P135). The % electron transition of drug molecule chromophores (such as phenyl) that enter the hydrophobic cavity (inclusion) vary induced by the high electron density of cyclodextrin hydrophobic cavity, which induced the changes of UV spectra.

The determination of system UV absorption is an effective method to identify the inclusion reaction. Paclitaxel UV absorption would significantly enhance with the increase of cyclodextrin concentration, suggesting that paclitaxel has a significantly strong inclusion with the cyclodextrin under the present invention.

Determination of Inclusion Stability Constant:

The inclusion stability constant Ka is used to determine the degree of inclusion and UV spectrophotometry is one of common methods to determine Ka. With the change of cyclodextrin concentrations (without absorption of cyclodextrin itself), the UV absorption of paclitaxel solution of constant concentration shows a regular change, and the relationship between cyclodextrin concentration (C) and UV absorbance (A) is obtained. From the relation curve of 1/C and 1/A, the first-level apparent stability constant Ka of cyclodextrin/paclitaxel inclusion can be quantitatively calculated. Meanwhile, the changes of Ka after adding ethanol are determined in the test, and the Ka values of different cyclodextrins are shown in Table 1.

TABLE 1

The first-level apparent stability constant Ka of cyclodextrin/paclitaxel ($M^{-1}$; 234 nm)

| Cyclodextrin | Ka | |
|---|---|---|
| | $H_2O$ | 60% EtOH |
| sulfobutyl-β-cyclodextrin | 5396 | 9367 |
| hydroxypropyl-sulfobutyl-β-cyclodextrin | 14121 | 19722 |
| hydroxypropyl-β-cyclodextrin | 1325 | 4646 |
| β-cyclodextrin | 413 | |

The results showed that, the cyclodextrin used in the present invention had a higher inclusion constant Ka, and the existence of ethanol significantly increased the Ka value (enhance the capacity of cyclodextrin inclusion), so ethanol had the effect of promoting inclusion instead of just a cosolvent. Generally, when organic solvents compete with the drugs for inclusion, ethanol would reduce the Ka value of drugs. Different from hydroxypropyl-β-cyclodextrin, the cyclodextrin/paclitaxel inclusion has a higher Ka value to produce a stable inclusion under the pure water condition, so after the inclusion forms, the ethanol should be removed as possible to obtain a more pure drug inclusion, which could decrease the impact of ethanol on the drug. For the present invention, the impact of ethanol on the paclitaxel inclusion is the technological basis for preparation of inclusion.

Preparation and validation f Inclusion

After adding appropriate amount of ethanol to make full inclusion, remove different proportions of sulfobutyl-β-cyclodextrin, hydroxypropyl-sulfobutyl-β-cyclodextrin and their mixture/paclitaxel solid inclusion after drying under reduced pressure. DTA test confirmed that the solid substance is inclusion rater than simple physical mixture. Taking sulfobutyl-β-cyclodextrin/paclitaxel (mass ratio of 25:1) as an example, it is analyzed and described as follows:

Four samples of paclitaxel, sulfobutyl-β-cyclodextrin, physical mixture of paclitaxel and sulfobutyl-β-cyclodextrin and inclusion were weighed, each for about 5 mg, to conduct differential scanning thermal analysis: reference: Al2O3, range: 50 μV, temperature rise range: 30° C.~400° C., heating rate 10° C./min, and the DTA pattern was obtained. The results showed that: for paclitaxel, a melting peak (decomposition) at 240° C.; for cyclodextrin, there is one dehydration endothermic peak and one phase transition peak at 70~90° C. and 250~270° C. respectively and one melting decomposition peak at about 360° C. For the physical mixture, the endothermic peak characteristics of cyclodextrin and paclitaxel maintained, while for the inclusion, the dehydration endothermic peak significantly weakened, phase transition peak basically disappeared and the positions (temperature) and shapes (thermal effect) of other peaks obviously changed, therefore, it indicated that the inclusion formed.

Residual Ethanol of the Inclusion:

Inclusion 1HNMR showed a weak ethanol methyl peak. According to the integral area ratio of ethanol methyl peak (t, δ=1.10941) and cyclodextrin characteristic peak (H-1 peak, d, □δ=5.18258~5.05405), the residual ethanol amount (%) of inclusions prepared was calculated, the results were shown in Table 2,

TABLE 2

Residual ethanol level of paclitaxel/cyclodextrin solid inclusion

| Batch Number of Inclusion | cyclodextrin* | Ratio of drug/cyclodextrin | Residual ethanol level (%) |
|---|---|---|---|
| 20060128 | a | 1:50 | 0.43 |
| 20060131 | b | 1:50 | 0.51 |
| 20060306 | a | 1:30 | 0.37 |
| 20060318 | b | 1:30 | 0.22 |
| 20060608 | b | 1:25 | 0.21 |
| 20060629 | a | 1:25 | 0.27 |
| 20060730 | a + b | 1:25:25 | 0.37 |
| 20060812 | b | 1:100 | 1.26 |

*a = sulfobutyl-β-cyclodextrin; b = hydroxypropyl-sulfobutyl-β-cyclodextrin.

The test showed that, although more ethanol was used in the preparation process, there was less residual ethanol after purification. For the inclusion prepared with a low proportion of cyclodextrin (less than 1:50), generally the residual ethanol level was less than 1.0%; even for the inclusion prepared with a higher proportion of cyclodextrin, the residual ethanol level was less than 2.0%. The significant reduction of residual ethanol level with strong volatility and irritation provided a favorable guarantee for improving the paclitaxel stability and reducing irritation and other side effects.

Inclusion Solubilization Test:

Standard curve: ethanol solution was used to prepare 0.225 mg/ml paclitaxel mother liquor and diluted with pure water into 0.25 μg/ml~2.25 μg/ml series solutions, then UV absorption A was measured under 234 nm. A standard curve was plotted by A and concentration C (mg/ml) (A=393.2 C−0.0123; r=0.9998).

Different concentrations of cyclodextrin solutions were prepared with pure water, added with the bulk drug paclitaxel and oscillated for 72 h at 25° C.±1° C., filtered and placed still. Appropriate amount of filtrate was fetched and diluted with pure water, then UV absorption values were measured at 234 nm to calculate the paclitaxel solubility from the standard curve, the results were shown in Table 3.

TABLE 3

Paclitaxel solubility in cyclodextrin solution

| cyclodextrin* (concentration %) | Solubility (mg/ml) | Solubilization multiples |
|---|---|---|
| 0 | 0.000589 | 1 |
| a (25) | 9.324 | 15540 |
| a (31) | 10.182 | 16971 |
| b (31) | 11.177 | 18629 |

*a = sulfobutyl-β-cyclodextrin; b = hydroxypropyl-sulfobutyl-β-cyclodextrin

Although high concentration of cyclodextrin solution (>50%) has a high solubilization, it has no practical application value. Therefore, solubilization test of cyclodextrin aqueous solution of concentration below 31% was conducted. The results showed that, the cyclodextrin adopted in the present invention has extremely strong solubilization on paclitaxel.

Stability of Samples:

The pharmaceutical composition stability, including chemical stability of drug and pharmaceutical stability of composition, is the basic element of pharmaceutical composition applications.

Solid Inclusion Stability

HPLC chromatographic conditions: chromatographic column ODS $C_{18}$ (250 mm×4.6 mm); mobile phase: methanol:water:acetonitrile (20:30:50); flow rate: 1.0 ml/min; detection wavelength: 228 nm; detection time: 30.00 min; detection sensitivity: 1.0000 AUFS.

Samples: Paclitaxel material; paclitaxel/sulfobutyl-β-cyclodextrin inclusion (a, mass ratio of 1:25); paclitaxel/hydroxypropyl-sulfobutyl-β-cyclodextrin inclusion (b, mass ratio of 1:25)

Paclitaxel material and inclusion were divided into three portions of test samples equally and were subject to light, high temperature and high humidity acceleration tests respectively:

1) Light Test

Samples were put in a sealed transparent container and then placed in an illumination box equipped with fluorescent light of 4500±500 LX illumination intensity for 5 days. Sampling inspection analysis was conducted, and the test results were compared with the samples of 0 day.

2) High Temperature Test

Samples were placed in a clean sealed container at temperature of 60° C. for 5 days. Sampling inspection analysis was conducted, and the test results were compared with the samples of 0 day.

3) High Humidity Test

Samples were placed in a sealed container of constant humidity at temperature of 25° C. and relative humidity of 90±5% for 5 days. Sampling inspection analysis was conducted, and the test results were compared with the samples of 0 day.

HPLC determination results see FIG. 3 and FIG. 4. All the test results see Table 4. Under the acceleration test conditions, the color of paclitaxel material became slightly darker and the level decreased significantly; the inclusion appearance had no color change, and the level decreased slightly without change of impurities. The results showed that, for the solid inclusion, the chemical property of paclitaxel is stable and the inclusion technology had a significant effect on improving the stability of paclitaxel.

TABLE 4

Sample Content Determination of 5-day Acceleration Test

| | Content (%) | | | |
|---|---|---|---|---|
| Sample | 0 day | Light | High temprature | High humidity |
| Paclitaxel material | 99.748 | 90.346 | 91.569 | 89.336 |
| Inclusion a | 99.746 | 97.035 | 96.476 | 96.141 |
| Inclusion b | 99.736 | 96.786 | 97.255 | 96.022 |

Inclusion Solution and Pharmaceutical Stability (1) Solution Stability:

Solid inclusions of mass ratio of 1:25 were prepared into 10 mg/ml solutions containing paclitaxel with saline solution and isotonic glucose solution respectively, diluted for 1~1000 times. After sterilization, the resulting solutions were prepared into different concentrations of injections, observed for 5 h~10 d in succession. The observation results of paclitaxel/hydroxypropyl-sulfobutyl-β-cyclodextrin inclusion saline dilution system stability were shown in Table 5.

TABLE 5

State of cyclodextrin/paclitaxel inclusion injection

| | Drug concentration | Solution State* | | | | | | | | |
|---|---|---|---|---|---|---|---|---|---|---|
| Dilution multiple | mg/ml | 0 h | 5 h | 10 h | 15 h | 20 h | 2 d | 4 d | 6 d | 10 d |
| 1 time | 5.00 | + | + | + | + | + | − | − | − | − |
| 10 times | 1.00 | + | + | + | + | + | + | + | + | + |
| 20 times | 0.50 | + | + | + | + | + | + | + | + | + |
| 50 times | 0.20 | + | + | + | + | + | + | + | + | + |
| 100 times | 0.10 | + | + | + | + | + | + | + | + | + |
| 500 times | 0.02 | + | + | + | + | + | + | + | + | + |
| 1000 times | 0.01 | + | + | + | + | + | + | + | + | + |

*+: Clarification without precipitation; −: generate precipitation or turbidity.

(2) Paclitaxel Stability Test in Solution (Assay)

Under the aforesaid HPLC chromatographic conditions, some paclitaxel materials and inclusions were fetched and dissolved with a mobile phase (pH=6.50), diluted for 100 times after 30 min ultrasonic wave treatment, placed still, and then the samples were taken to measure HPLC chromatogram at 0 h, 2 h, 4 h, 6 h, 8 h. The sample solutions had stable chemical properties and the content was basically unchanged.

TABLE 6

Changes of sample content in aqueous solution with time

| | Content (%) | | | | |
|---|---|---|---|---|---|
| Sample | 0 h | 2 h | 4 h | 6 h | 8 h |
| Paclitaxel material | 99.745 | 99.700 | 99.577 | 99.648 | 99.608 |
| Inclusion a | 99.736 | 99.740 | 99.717 | 99.687 | 99.702 |
| Inclusion b | 99.748 | 99.718 | 99.630 | 99.627 | 99.605 |

Hemolysis Test:

(References: State Food and Drug Administration "Guiding principle of chemical drug irritation, allergic and hemolytic research technology", 2005, 3, 18; State Drug Administration "Technical requirements of traditional Chinese medicine injection study", 1999, 11, 12)

There is significant difference of the hemolysis between the inclusion saline solution and existing paclitaxel formulation. The diluted solid inclusion solution has a slight hemolysis; while the existing paclitaxel formulation has a hemolysis as high as 15% even diluted to a concentration of 0.06 mg/ml. The results see FIG. 5.

In Vivo Anti-Tumor Effect:

Male Kunming mice weighed 20±2 g were inoculated subcutaneously with 0.2 ml of $1\times10^7$/ml $S_{180}$ cells ($2\times10^6$ cells) in a solid tumor model and were subject to intraperitoneal administration of paclitaxel and paclitaxel/cyclodextrin inclusion sample solution for 7 days. Under the test conditions, 5 mg/kg dose of paclitaxel/cyclodextrin inclusion has an anti-tumor rate as high as 94.69%, significantly higher than that of non-inclusion paclitaxel (anti-tumor rate of 82.77%); both paclitaxel and paclitaxel/cyclodextrin inclusion can reduce the animal body weight, but the weight loss of animals of the paclitaxel group was greater than those of the inclusion group. The results suggested that, after paclitaxel inclusion, the anti-tumor activity enhanced while the side effects reduced.

ADVANTAGES OF THE INVENTION

The inclusion significantly improves the solubility of paclitaxel (up to 10 mg/ml and above). After dilution, the solution can maintain clear and stable for a long time, with low hemolysis, less side effect and good pharmaceutical activity.

After inclusion of paclitaxel and cyclodextrin, the solid and liquid samples have stable content, small proportion of drug/cyclodextrin, low dosage of cyclodextrin in the formulation, suitable for clinical use.

The inclusion in the present invention has less residual organic solvents, conducive to improve the medication safety.

The preparation method is simple, easy to operate, low cost without environmental pollution. The inclusion has stable property, good compatibility with other pharmaceutical excipients, suitable for preparation of formulations.

The injections prepared by inclusions contain no corrosive ingredients, no poisons, convenient for clinical use and high practicability.

DETAILED DESCRIPTION OF THE INVENTION

EXAMPLE 1

Figure 1:
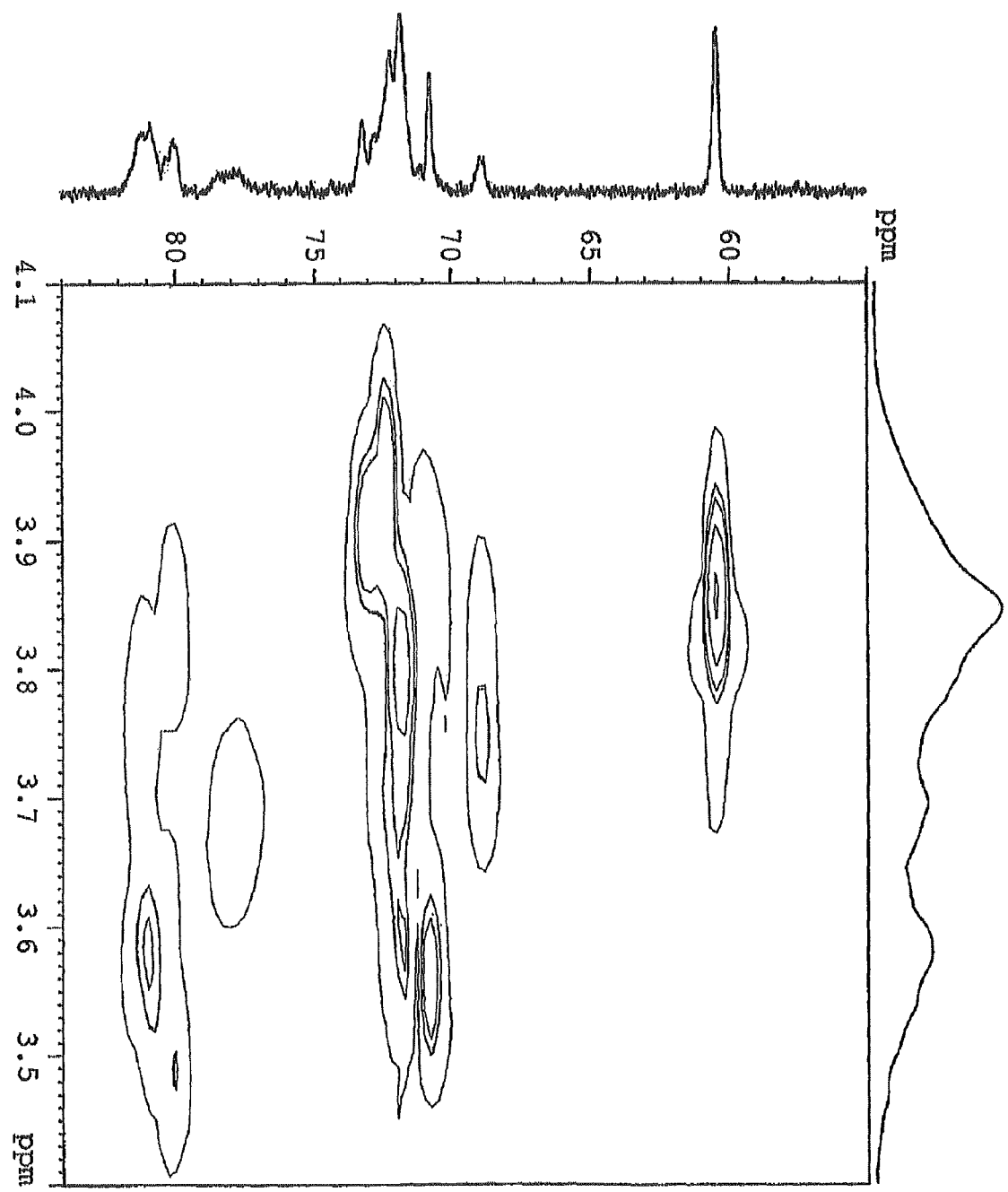
FIG. 1: Paclitaxel/sulfobutyl-β-cyclodextrin inclusion H,COSY, with mass ratio of 1:9 (solvent $D_2O$, δ4.1~3.4 part)
Figure 2:
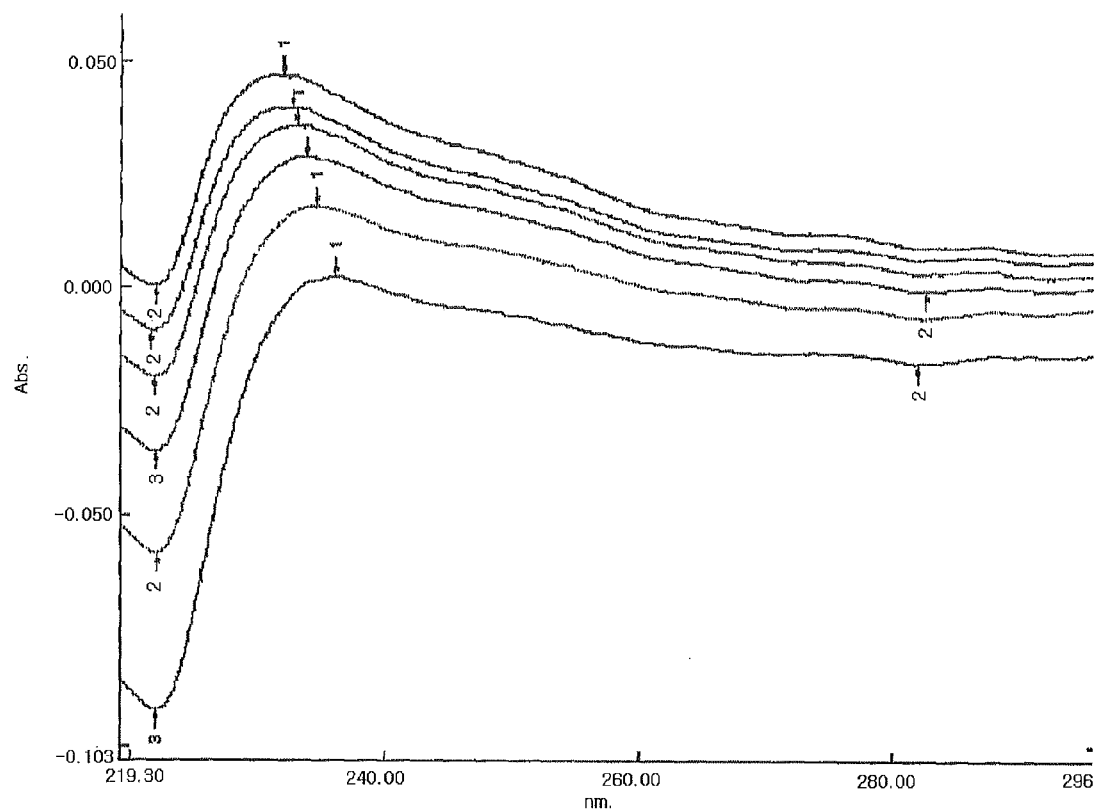
FIG. 2: paclitaxel UV absorption scanning under different concentrations of hydroxypropyl-sulfobutyl-β-cyclodextrin in aqueous solution (210 nm ~296 nm)
Figure 3:
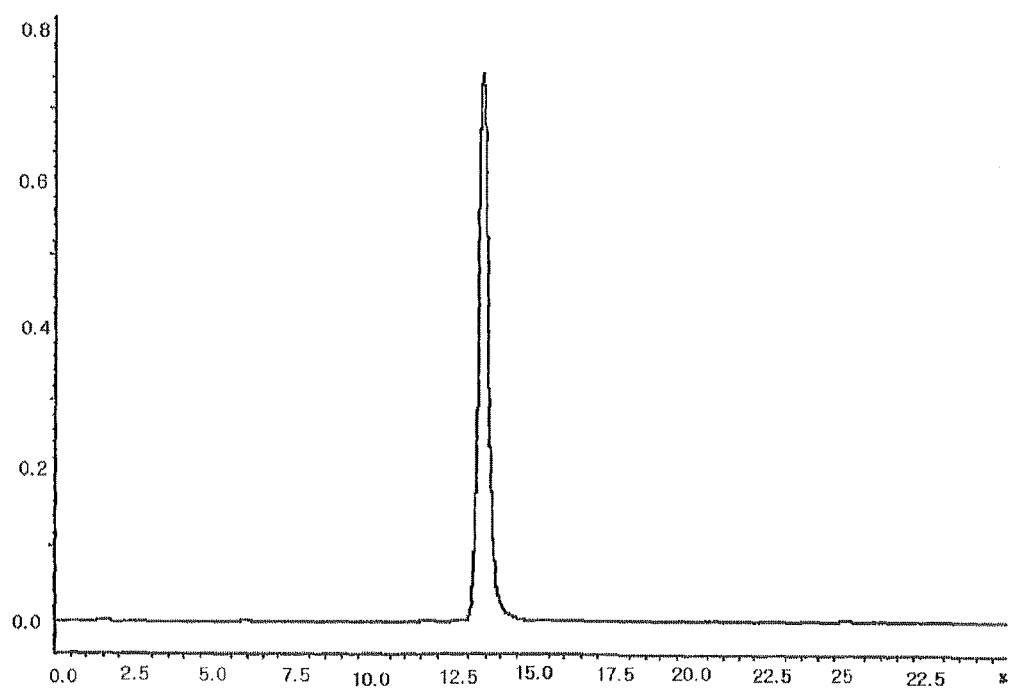
FIG. 3: HPLC chromatogram of paclitaxel/hydroxypropyl-sulfobutyl-β-cyclodextrin inclusion high temperature test (5 d)
Figure 4:
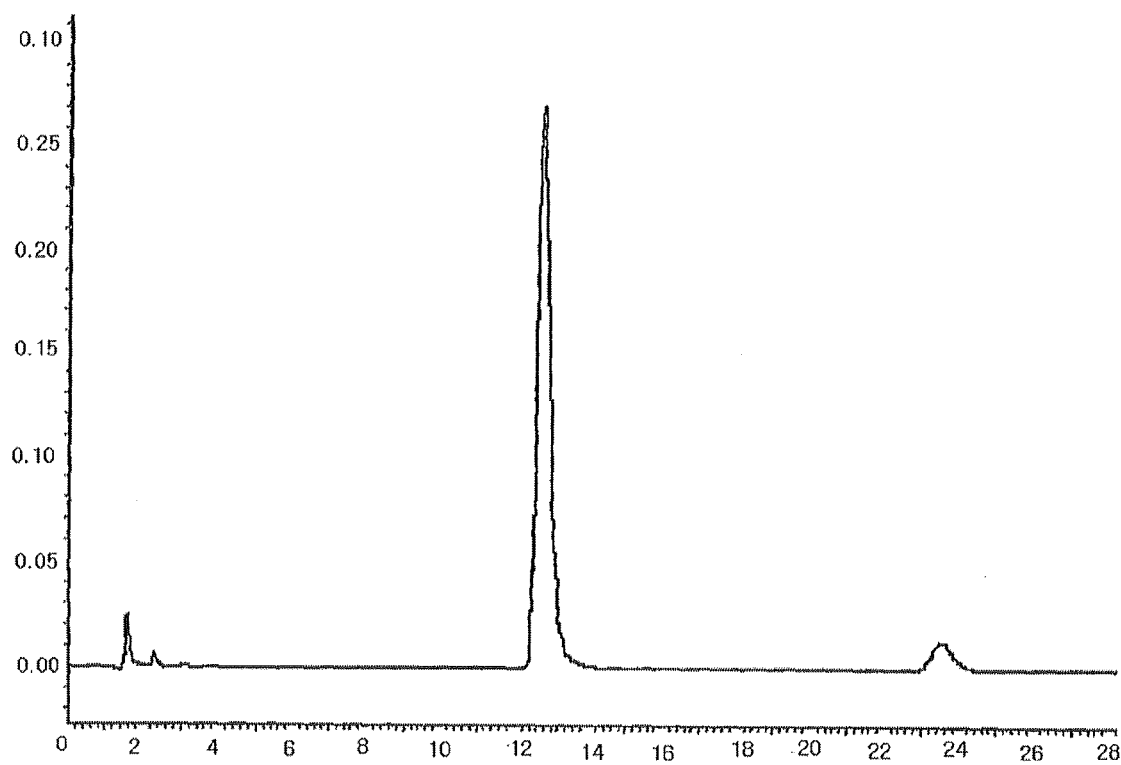
FIG. 4: HPLC chromatogram of paclitaxel material high-temperature test (5 d)
Figure 5:
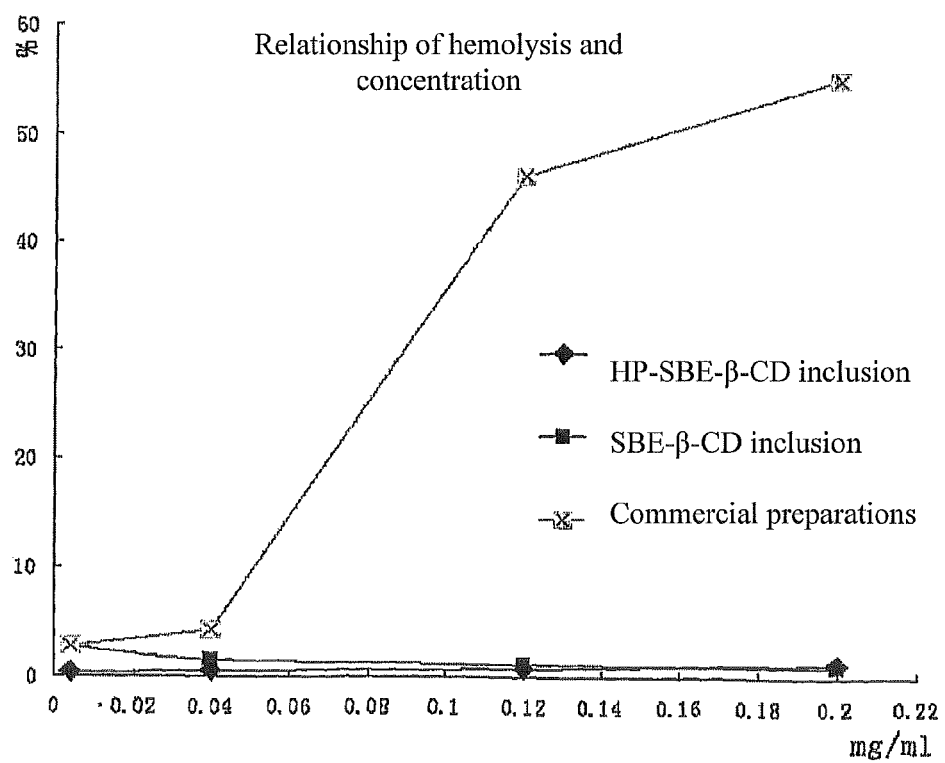
FIG. 5: Commercial paclitaxel formulations, paclitaxel/hydroxypropyl-sulfobutyl-μ-cyclodextrin (HP-SBE-β-CD) inclusion and paclitaxel/sulfobutyl-β-cyclodextrin (SBE-β-CD) inclusion solutions diluted with normal saline solution and paclitaxel concentration-hemolysis curve

3 g hydroxypropyl-sulfobutyl-β-cyclodextrin was mixed with 6 ml pure water, then added dropwise slowly with a solution prepared by 120 mg paclitaxel and 3 ml ethanol while stirring. After fully mixed until complete dissolution, the resulting mixture was filtered through microporous membrane of 0.2~0.4 μm. The ethanol was removed from the filtrate at 65° C. under reduced pressure. After sterilization treatment, the water was also removed under reduced pressure until dry, and then the resulting solid product was dried for 48 h under reduced pressure giving a white solid inclusion. All parameters see FIG. 1-FIG. 5.

The above powdered inclusion 780 mg (containing 30 mg paclitaxel) was mixed and diluted with 250 ml of normal saline injection to a liquid inclusion composition before used for injection.

EXAMPLE 2

The procedure was carried out basically the same as example 1, but wherein, 4.5 g hydroxypropyl-sulfobutyl-β-cyclodextrin was mixed with 15 ml pure water. The weight of paclitaxel was 30 mg.

EXAMPLE 3

The procedure was carried out basically the same as example 1, but wherein, the weight of paclitaxel was 300 mg.

EXAMPLE 4

The procedure was carried out basically the same as example 1, but wherein, the cyclodextrin was sulfobutyl-β-cyclodextrin.

EXAMPLE 5

The procedure was carried out basically the same as example 2, but wherein, the cyclodextrin was sulfobutyl-β-cyclodextrin.

EXAMPLE 6

The procedure was carried out basically the same as example 3, but wherein, the cyclodextrin was sulfobutyl-β-cyclodextrin.

EXAMPLE 7

The procedure was carried out basically the same as example 1, but wherein, the cyclodextrin was the mixture of sulfobutyl-β-cyclodextrin and hydroxypropyl-sulfobutyl-β-cyclodextrin in a mass ratio of 1:1.

EXAMPLE 8

The procedure was carried out basically the same as example 2, but wherein, the cyclodextrin was the mixture of sulfobutyl-β-cyclodextrin and hydroxypropyl-sulfobutyl-β-cyclodextrin in a mass ratio of 1:50.

EXAMPLE 9

The procedure was carried out basically the same as example 3, but wherein, the cyclodextrin was the mixture of sulfobutyl-β-cyclodextrin and hydroxypropyl-sulfobutyl-β-cyclodextrin in a mass ratio of 50:1.

EXAMPLE 10

The procedure was carried out basically the same as example 1, but, cyclodextrin and paclitaxel were mixed with 6 ml pure water first, added dropwise with ethanol slowly until the system was completely dissolved.

EXAMPLE 11

The procedure was carried out basically the same as example 1, but, the resulting powdered inclusion was diluted with isotonic concentrations of glucose injection.

EXAMPLE 12

The procedure was carried out basically the same as example 1, but, the resulting powdered inclusion was diluted with isotonic concentrations of fructose injection.

We claim:

1. A pharmaceutical composition comprising:
    a cyclodextrin/paclitaxel inclusion which consists of paclitaxel, cyclodextrin and a pharmaceutically acceptable excipient;
    wherein a mass ratio of paclitaxel to cyclodextrin is 1:10~150;
    wherein the cyclodextrin is hydroxypropyl-sulfobutyl-β-cyclodextrin,; and
    wherein a stability constant of the cyclodextrin/paclitaxel inclusion is $Ka=5396M^{-1}-14121M^{-1}$.

2. The pharmaceutical composition according to claim 1, wherein, a preparation method of the pharmaceutical composition is as follows:
    a solution of paclitaxel in ethanol is added dropwise to a pure water solution of hydroxypropyl-sulfobutyl-β-cyclodextrin while stirring;
    the resulting mixture is filtered through a microporous membrane of 0.2~0.4 μm after being dissolved; and
    the ethanol is removed under reduced pressure, then water is also removed under reduced pressure, wherein the resulting product is at least one of dried giving a solid inclusion and the ethanol is removed under reduced pressure giving a liquid inclusion.

3. The pharmaceutical composition according to claim 2, wherein an ethanol content of said solid inclusion is less than 2%.

4. A preparation method of the pharmaceutical composition comprising the cyclodextrin/paclitaxel inclusion according to claim 1 is as follows:
    a solution of paclitaxel in ethanol is added dropwise to an aqueous solution of hydroxypropyl-sulfobutyl-β-cyclodextrin while stirring;
    the resulting mixture is filtered through a microporous membrane of 0.2~0.4 μm after being dissolved; and
    the ethanol is at least one of:
        removed under reduced pressure giving a liquid inclusion; and
        the ethanol is removed under reduced pressure then the water is removed under reduced pressure wherein the resulting product is dried giving a solid inclusion;
    wherein the ethanol level of resulting inclusion is less than 2%.

5. The preparation method according to claim 4, wherein, the specific steps are as follows:
    the paclitaxel and cyclodextrin in a mass ratio of 1:25 are used to prepare an aqueous solution of cyclodextrin;
    the solution prepared with hydroxypropyl-sulfobutyl-β-cyclodextrin and 2~10 times of pure water (in-weight) is added to the mixed solution prepared by paclitaxel and appropriate amount of ethanol, while at least one of heating and stirring at room temperature and at a temperature of 25~65° C.;
    after the inclusion forms, filtered through a microporous membrane of 0.2~0.4 μm;
    then the ethanol is removed under reduced pressure to give a liquid inclusion;
    pressure is continued to be reduced until water is removed; and
    wherein the resulting product is dried under a vacuum condition to give the solid inclusion.

6. A pharmaceutical composition comprising:
    a cyclodextrin/paclitaxel inclusion which consists of paclitaxel, cyclodextrin and a pharmaceutically acceptable excipient;
    wherein a mass ratio of paclitaxel to cyclodextrin is 1:10~24;
    wherein the cyclodextrin is sulfobutyl-β-cyclodextrin; and
    wherein a stability constant of the cyclodextrin/paclitaxel inclusion is $Ka=5396M^{-1}-14121M^{-1}$.

7. The pharmaceutical composition according to claim 6, wherein, a preparation method of the pharmaceutical composition is as follows:
    a solution of paclitaxel in ethanol is added dropwise to a pure water solution of sulfobutyl-β-cyclodextrin while stirring;
    the resulting mixture is filtered through a microporous membrane of 0.2~0.4 μm after being dissolved; and
    the ethanol is removed under reduced pressure, then water is also removed under reduced pressure, wherein the resulting product is at least one of dried giving a solid inclusion and the ethanol is removed under reduced pressure giving a liquid inclusion.

8. The pharmaceutical composition according to claim 7, wherein an ethanol content of said solid inclusion is less than 1%.

9. A preparation method of the pharmaceutical composition comprising the cyclodextrin/paclitaxel inclusion according to claim 6 is as follows:
    a solution of paclitaxel in ethanol is added dropwise to an aqueous solution of hydroxypropyl-sulfobutyl-β-cyclodextrin while stirring;
    the resulting mixture is filtered through a microporous membrane of 0.2~0.4 μm after being dissolved; and
    the ethanol is at least one of:
        removed under reduced pressure giving a liquid inclusion; and
        the ethanol is removed under reduced pressure then the water is removed under reduced pressure wherein the resulting product is dried giving a solid inclusion;
    wherein the ethanol level of resulting inclusion is less than 1%.

* * * * *

UNITED STATES PATENT AND TRADEMARK OFFICE
CERTIFICATE OF CORRECTION

PATENT NO. : 8,426,385 B2
APPLICATION NO. : 12/440792
DATED : April 23, 2013
INVENTOR(S) : Ren et al.

Page 1 of 4

It is certified that error appears in the above-identified patent and that said Letters Patent is hereby corrected as shown below:

On the Title Page, Item [57] Abstract

Line 8, after "is" delete "Ka=5396M-1-1412M-1" and insert --$K_a=5396M^{-1}-1412M^{-1}$--

On the Title Page, Item [56] Other Publications, Page 2, Column 2

Office Action #1, Line 1, after "Apr." delete "14" and insert --18--

Office Action #2, Line 1, after "Aug." delete "24" and insert --23--

Office Action #3, Line 1, after "Date" delete "Jan. 25, 2012" and insert --Sep. 12, 2012--

Office Action #3, Line 2, after "filed" delete "Mar. 11, 2009" and insert --Jan. 14, 2013--

In the Specifications

Column 1

Line 25, after "fat-solubility" delete "(log P.0/w=3.5)" and insert --(logP o/w=3.5)--

Line 37, after "oral" delete "taking" and insert --administration--

Line 63, after "prevent" delete "from" and insert --a--

Column 2

Line 7, after "drug" delete "carrier" and insert --carriers--

Signed and Sealed this
Eleventh Day of March, 2014

Michelle K. Lee
*Deputy Director of the United States Patent and Trademark Office*

CERTIFICATE OF CORRECTION (continued)  Page 2 of 4
U.S. Pat. No. 8,426,385 B2

Line 18, after "used to" delete "paclitaxel preparations improvement" and insert --improve paclitaxel preparations--

Line 24, after "used" delete "to" and insert --in--

Line 33, after "volume," delete "researches show" and insert --research shows--

Line 47, after "Where," delete "Rm" and insert --$R_m$--

Line 50, after "value" delete "Rmo" and insert --$R_{m0}$--

Line 52, after "then" delete "Rm=Rmo" and insert --$R_m=R_{m0}$--

Line 53, delete "Rmo" and insert --$R_{m0}$--

Line 56, after "maximum" delete "Rmo" and insert --$R_{m0}$--

Column 3

Line 3, after "and" delete "7965M⁻" and insert --$7965M^{-1}$--

Column 4

Line 50, after "is" delete "Ka" and insert --$K_a$--

Line 62, after "0.2~0.4" delete "um" and insert --μm--

Column 5

Line 60, after "0.2~0.4" delete "um" and insert --μm--

Column 6

Line 13, after "0.2-0.4" delete "um" and insert --μm--

Line 20, after "prepared" delete "has less side effect of hemolysis" and insert --exhibits less side effects of--

Lines 56-57, after "one" delete "of common" and insert --of the common--

Line 57, after "determine" delete "Ka" and insert --$K_a$--

Line 63, after "constant" delete "Ka" and insert --$K_a$--

Line 65, after "of" delete "Ka" and insert --$K_a$--

Line 66, after "and the" delete "Ka" and insert --$K_a$--

Column 7

Table 1 title, after "constant" delete "Ka" and insert --$K_a$--

Table 1, Line 6, delete "Ka" and insert --$K_a$--

Line 16, after "constant" delete "Ka" and insert --$K_a$--

Line 17, after "the" delete "Ka" and insert --$K_a$--

Line 21, after "the" delete "Ka" and insert --$K_a$--

Line 31, after "validation" delete "f" and insert --of--

Line 38, after "inclusion" delete "rater" and insert --rather--

Line 45, after "30°" delete "C." and insert --C--

Line 45, after "400°" delete "C." and insert --C--

Line 46, after "10°" delete "C." and insert --C--

Line 48, after "240°" delete "C." and insert --C--

Line 50, after "70~90°" delete "C." and insert --C--

Line 50, after "250~270°" delete "C." and insert --C--

Line 62, after "Inclusion" delete "1HNMR" and insert --1H NMR--

Line 65, delete "d☐δ" and insert --d,δ--

Column 8

Line 37, after "25°" delete "C." and insert --C--

Line 37, after "1°" delete "C." and insert --C--

Column 9

Line 39, after "60°" delete "C." and insert --C--

Line 43, after "25°" delete "C." and insert --C--

CERTIFICATE OF CORRECTION (continued)
U.S. Pat. No. 8,426,385 B2

Table 4, Line 63, delete "temprature" and insert --temperature--

Column 10

Table 6, Line 47, delete "paclitaxelmaterial" and insert --paclitaxel material--

Column 11

Line 63, after "65°" delete "C." and insert --C--

In the Claims

Column 13

Line 16, Claim 1, after "is" delete "Ka" and insert --$K_a$--

Column 14

Line 4, Claim 5, after "25~65°" delete "C." and insert --C--

Line 21, Claim 6, after "is" delete "Ka" and insert --$K_a$--